United States Patent [19]

Giuliani et al.

[11] Patent Number: 4,954,129
[45] Date of Patent: Sep. 4, 1990

[54] HYDRODYNAMIC CLOT FLUSHING

[75] Inventors: David Giuliani, Mercer Island, Wash.; Gerald G. Vurek, Mt. View, Calif.

[73] Assignee: Abbott Laboratories, Abbott Park, Ill.

[21] Appl. No.: 224,074

[22] Filed: Jul. 25, 1988

[51] Int. Cl.$^5$ .................. A61M 5/00; A61M 25/00
[52] U.S. Cl. .................. 604/53; 604/131; 604/264; 604/280; 604/93
[58] Field of Search .......... 604/53, 52, 93, 131, 604/164, 266, 264; 128/DIG. 12, 4, 6

[56] References Cited

U.S. PATENT DOCUMENTS

| | | | |
|---|---|---|---|
| 3,916,892 | 11/1975 | Latham, Jr. ................ | 604/83 |
| 4,540,406 | 9/1985 | Miles ........................ | 604/269 |
| 4,738,265 | 4/1988 | Ritchart et al. ............ | 128/673 |
| 4,840,623 | 6/1989 | Quackenbush ............ | 604/280 |

*Primary Examiner*—Stephen C. Pellegrino
*Attorney, Agent, or Firm*—Christensen, O'Connor, Johnson & Kindness

[57] ABSTRACT

A process for flushing clots from an intravascular probe including the steps of positioning a catheter assembly in a blood vessel and then delivering a flushant through the catheter and past the probe at two rates. The flushant is first delivered at a continual rate to maintain the catheter substantially free of blood clots. Periodically, a pulse of flushant is delivered at a second flow rate that is higher than the continual rate that is effective to clear the probe of incipient clots. The hydrodynamic clot flushing system includes a cather insertable within an arterial or venous blood vessel, the cather having an internal axial bore for conducting fluid and in which a probe is slidably received. A valve delivers a flushant through the internal axial bore of the catheter and around the probe at two selected rates. A plurality of radially arrayed ribs formed on either the internal wall of the catheter or the outside of the probe or both hold the probe away from the wall and provide fluid channels for conducting flushant to the probe tip.

17 Claims, 2 Drawing Sheets

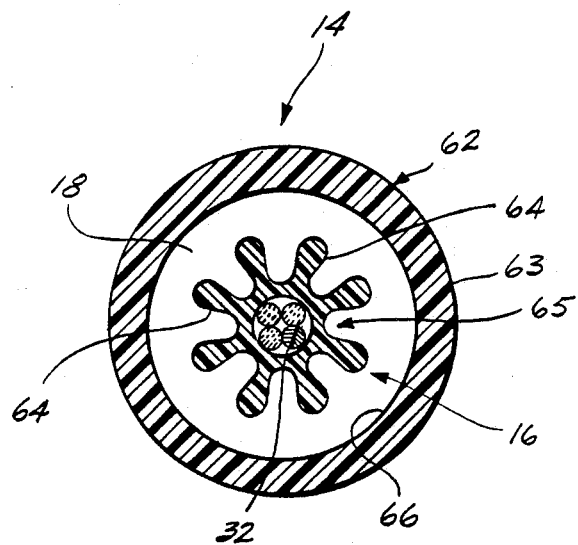
Fig. 2.
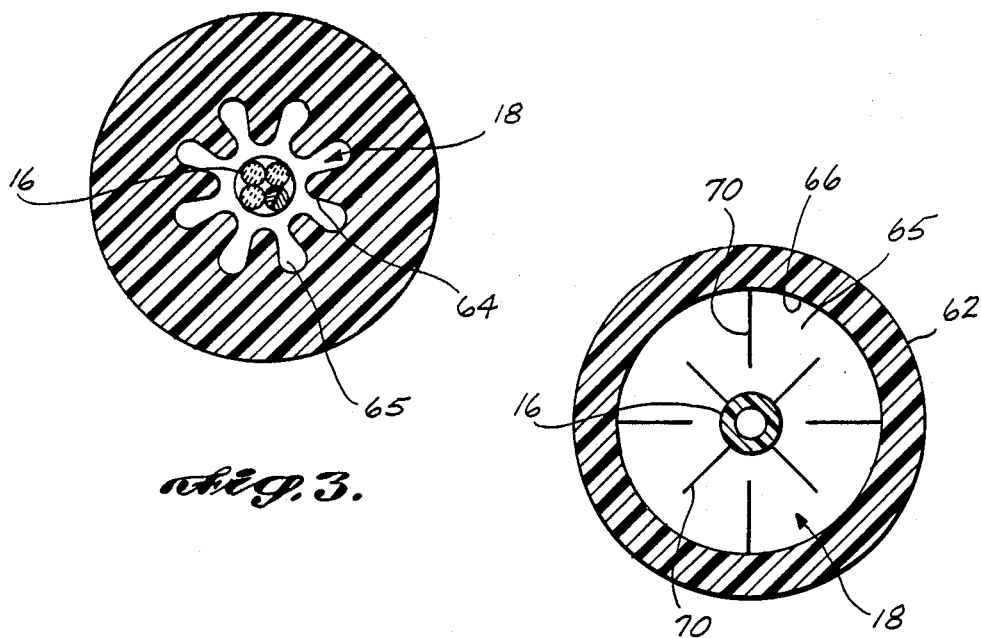
Fig. 3.
Fig. 4.

HYDRODYNAMIC CLOT FLUSHING

TECHNICAL FIELD

The present invention relates to medical devices employing hydraulic flushing and, more particularly, to hydrodynamic clot flushing for maintaining the tip of an intravascular probe clear of thrombi and other clotting material.

BACKGROUND OF THE INVENTION

Indwelling probes have been proposed for measuring various physiological parameters. For example, sensors on the tips of the probe have been designed to measure the partial pressures of carbon dioxide, oxygen, and pH (frequently referred to as the "blood gases"). In use, the sensors of such probes are positioned at or slightly beyond the distal end of a conventional hypodermic needle inserted within the arterial or venous bloodstream. A limitation to the accuracy of these sensors is the formation of clotting material such as thrombi or blood clots on or near the probe tips. Such clots can form within ten minutes to several hours following in vivo insertion of the probe. These clots in turn metabolize and create a microenvironment around the sensors that affect the accuracy of the sensors. In practice, sensors surrounded by such clots measure lower pH (more acidic) and higher $pCO_2$ ("partial pressure of $CO_2$") than when such clots are not present.

Several methods have been used in the art to overcome such problems. Probes have been coated with antithrombogenic materials, such as heparin, in an attempt to impair clot formation. Because heparin works best in relatively slow velocity conditions, it is ineffective in the high-velocity arterial system. Furthermore, heparin coatings tend to wear off with blood exposure, thereby becoming less effective over time.

Another technique to minimize and control clot formation is to deliver a supply of liquid or flushant at a very slow rate that is sufficient to flush the lumen or bore of the catheter to prevent clots from forming within the needle bore. One difficulty with this method is that a probe generally will lie tangent to one side of the catheter's exit orifice. As a result, the flushant will be diverted to the opposite side of the exit orifice, thereby minimizing the effectiveness of the flush in the region of the probe-catheter tangency. Consequently, clots of large size can eventually form around the probe and compromise the reliability of the sensor. Increasing the concentration of the flushant to prevent or dissolve these clots causes unacceptable errors in sensor performance. Furthermore, probes projecting beyond the end of the catheter will not receive the benefit of the flushant because the force of the blood flow will wash the flushant away. Thus, there is a need for a flushing system that can minimize and control clot formation without impairing sensor performance.

SUMMARY OF THE INVENTION

The invention provides a process for flushing clots from an intravascular probe. The process includes the steps of positioning a catheter assembly in a blood vessel, and then delivering a flushant through the catheter and past the probe. The catheter assembly includes a catheter segment having an internal axial bore that is fitted substantially throughout with an intravascular probe. The flushant is delivered at a continual rate sufficient to maintain the catheter bore substantially free of blood clots. Periodically, a pulse of flushant is delivered at a higher flow rate through the catheter bore that is effective to clear the probe of incipient clots. The continual rate of flushant delivery should be less than about 5% of the velocity of the blood in the blood vessel in which the catheter is inserted. The rate of the pulsed flushant is preferably in the range of from about 6 to about 50 times the blood flow velocity, e.g., in the range of about 100 cm per second to about 600 cm per second. The period of the high-velocity pulse can be in the range of about once every 10 minutes to about once every 2 hours.

The invention also provides a hydrodynamic clot flushing system for removing incipient blood clots from an intravascular probe. The system includes a catheter insertable within an arterial or venous blood vessel, the catheter having an internal axial bore for conducting fluid and in which a probe is slidably received. The system further includes a means for delivering a flushant through the internal axial bore of the catheter and around the probe at two rates, at a first flow rate effective to maintain the internal axial bore of the catheter substantially free or clear of blood clots and for delivering periodic pulses of flushant at a higher flow rate that is effective to substantially clear the probe of incipient clots.

The subject system also comprises means for centering the probe within the internal axial bore of the catheter. The centering means can include a plurality of radially arrayed ribs formed either on the internal wall of the catheter or on the outside of the probe or on both for holding the probe away from the wall of the catheter while providing fluid channels for conducting flushant to the probe tip.

BRIEF DESCRIPTION OF THE DRAWINGS

The foregoing and other features of this invention will become more readily appreciated as the same becomes better understood by reference to the following detailed description when taken in conjunction with the accompanying drawings wherein:

FIG. 2 is a cross-sectional view taken along line 2—2 in FIG. 1 showing a ribbed probe tip of the invention;

FIG. 3 is an alternative cross-sectional view of FIG. 2 showing a ribbed catheter bore of the invention; and FIG. 4 is an alternative cross-sectional view of FIG. 2 showing a ribbed catheter bore and ribbed probe of the invention.

DESCRIPTION OF THE PREFERRED EMBODIMENT

Figure 1:
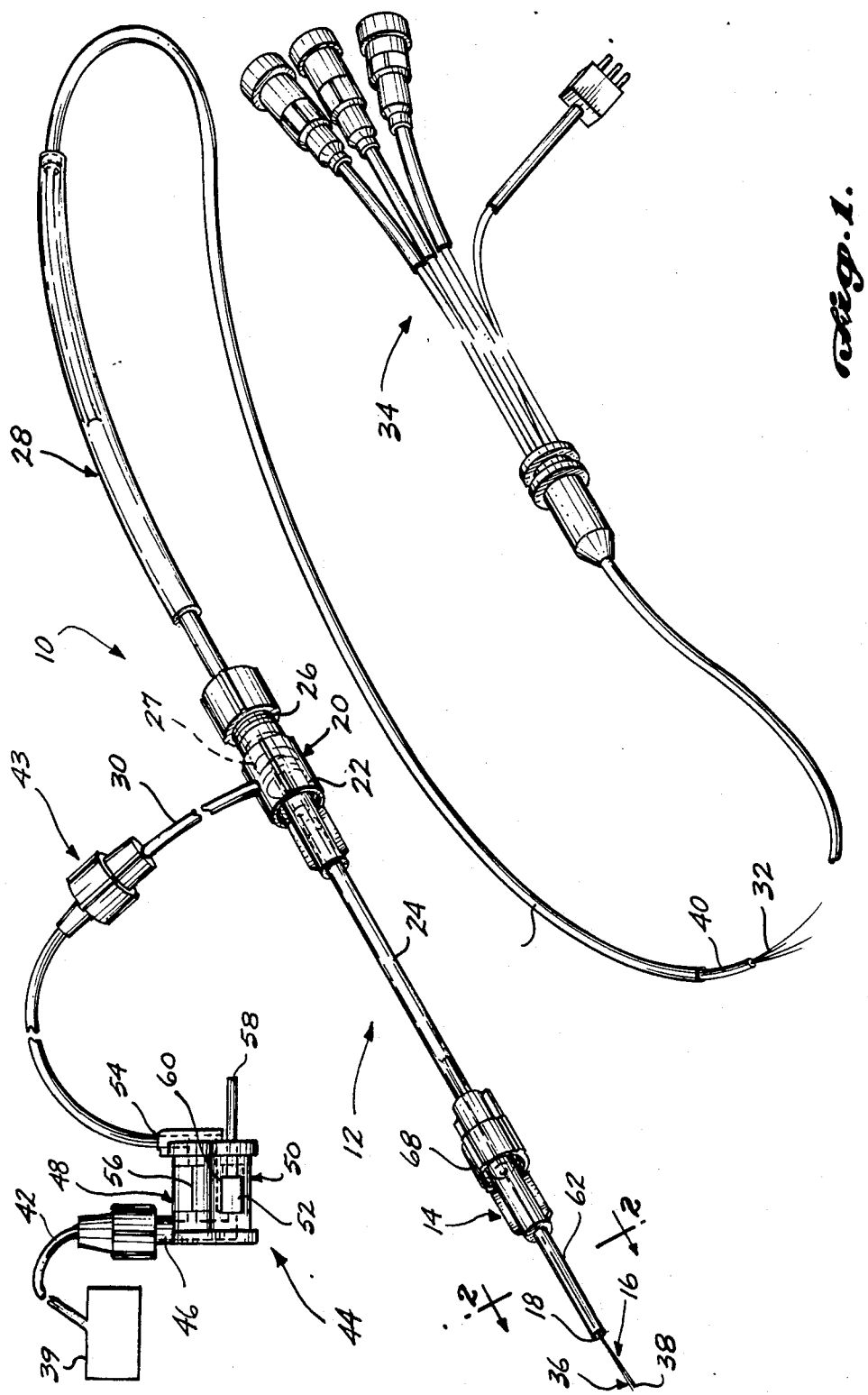
FIG. 1 is an isometric view of a representative hydrodynamic clot flushing system formed in accordance with the invention.

Referring initially to FIG. 1, the hydrodynamic clot flushing system 10 includes an intravascular delivery device 12 coupled to a catheter 14 for inserting and withdrawing a probe 16 through the internal axial bore 18 of the catheter 14. The intravascular delivery device 12 is disclosed in a co-pending U.S. patent application Ser. No. 162,476, filed on Mar. 1, 1988, entitled "Intravascular Delivery Device". Applicant incorporates herein by reference the subject matter of the above-referenced patent application.

In the illustrated embodiment of FIG. 1, the intravascular delivery device 12 includes a bifurcated fitting 20 having a female end 22 connected to a flexible guide tube 24 that in turn is coupled to the catheter 14. The fitting 20 also has a male end 26 that is attached to a delivery assembly 28. A side port 30 depends from the fitting 20 to allow the flow of fluids to and from the fitting 20, the guide tube 24 and the catheter 14. A seal 27 located inside the male end 26 of the fitting 20 prevents the flow of fluids into the delivery assembly 28, as is more fully described in the above-referenced copending application.

The probe 16 may be composed of one or more thermocouple wire pair strands or fiber-optic light strands 32, or a combination thereof, all encased in a protective sheath 40. The strands 32 terminate at a proximal end with one or more connectors 34 that are adapted to interface with signal monitoring and processing equipment (not shown). The exposed tips 36 at the distal end have sensors 38 thereon for measuring blood gases and other selected parameters. Usually, the probe 16 is advanced through the catheter to the point where the sensor(s) 38 are even with or project beyond the opening of the bore 18 of the catheter 14. In one embodiment, the probe is advanced 0.1 millimeter to 5 millimeters beyond the catheter bore 18 opening.

In order to prevent clots from forming within the internal axial bore 18 of the catheter 14 and around the sensor(s) 38 on the tip 36 of the probe 16, a flushant, preferably in the form of a saline solution containing an anti-coagulent such as heparin, is introduced through the side port 30. The flushant may be supplied by either a conventional pressure bag and flow control valve 44, or by an infusion pump, illustrated schematically as box 39, through a delivery line 42 that can be coupled to the side port 30 through a connector 43. In the representative embodiment, the flow control valve 44 includes an entry port 46, a low velocity chamber 48, a high velocity chamber 50 with a plug 52, and an exit port 54. Flushant enters the valve 44 through the entry port 46 and passes through a restricted passageway 56 in the low velocity chamber 48 to the exit port 54. The plug 52 in the high velocity chamber 50 has a tail 58 that projects outside the valve 44. Pulling of the tail 58 causes the plug 52 to constrict in diameter, thereby unplugging an enlarged passageway 60 in the high velocity chamber 50 to increase the flow rate of the flushant. It is to be understood that flow control may be achieved in other ways, such as a simple pinching of the delivery line 42 or through sophisticated electromechanical valves.

Small clots, i.e., those of approximately 1 cubic millimeter or less, may form, providing a basis for the formation of larger clots. In order to remove these incipient clots, the plug 52 is pulled via the tail 58 to release a pulse of high velocity flushant through the high velocity chamber 50. The pulse of flushant will be of sufficient velocity, as discussed more fully below, to completely clear the catheter bore 18 and the probe tip 36 of incipient clots.

FIG. 2 is a cross-sectional illustration of the catheter 14 showing a preferred ribbed embodiment of the probe 16. The catheter 14 includes the tube 62 having a wall 63 of generally circular cross-sectional shape defining the internal axial bore 18. Disposed within the internal axial bore 18 is the probe 16. Surrounding the strands 32 in the probe 16 is a sheath 40 that has a plurality of radially extending ribs 64 that lie substantially parallel to the longitudinal axis of the catheter's internal axial bore 18. The ribs 64 are disposed within the distal region of the probe 16 that slides within the catheter 18 and coact with the internal wall of the catheter tube 62 to center the probe 16 within the catheter bore 18. Channels 65 are formed between the ribs 64 to direct flushant through the catheter bore 18 and around and past the sheath 40 to prevent the formation of clots within the catheter 14 and to centralize the probe sheath 40 both in the catheter tube 62 and in the blood vessel to improve the flushing effect and prevent the sensor(s) from contacting the blood vessel walls.

The ribs 64 are shown having a semicircular cross-sectional shape; however, they may have other cross-sectional shapes such as square, pointed, or other suitable configuration that will centralize the probe 16 without impeding the flow of flushant. Although the ribs 64 are shown formed on the probe sheath 40, stabilizing ribs or fins may alternatively be formed on the inside surface 66 of the catheter tube 62 as shown in FIG. 3. In addition, FIG. 4 illustrates another embodiment wherein ribs 70 and channels 65 are radially positioned around the inside surface 66 of the catheter tube 62 and on the probe 16 and axially arranged along the axis of the catheter tube 62 to center the probe 16 within the catheter bore 18.

In operation, a needle is typically inserted through the catheter 14 and the catheter and needle assembly is then inserted into a blood vessel. The probe 16 is calibrated by coupling it to a manifold and delivering a flushant having parameters of known properties similar to those being measured past the probe tip 36. The monitoring equipment is then adjusted to reflect an accurate reading from the sensor(s) 38. After calibration, the flow control valve 44 is coupled to the side port 30 as illustrated in FIG. 1. A pressurized bag of infusion pump 39 is coupled to the entry port 46. The intravascular delivery device 12 is then attached to the catheter 14 through the flexible guide tube 24 by a connector 68. The delivery assembly 28 is used to advance the probe 16 through the catheter 14 until the probe tip 36 is at or slightly past the distal end of the catheter 14, approximately 0.1 to 5 millimeters, and projecting into the bloodstream. In most applications, the catheter 14 is inserted into the blood vessel such that the probe 16 is advanced upstream with respect to the directional flow of the blood.

After in vivo insertion, a saline solution is then supplied to the entry port 46 and allowed to flow through the low velocity chamber 48 of the valve 44 and into the catheter 14 at a continual rate. The flushant may be a conventional isotonic saline solution having 3 to 20 units per milliliter of heparin. Ideally, the ratio of the continual rate of flushant flow to the velocity of blood flowing in the blood vessel is less than 5%. At this flow rate, the effect of the buffering solution on the readings of the probe sensor(s) 38 is minimal, yet sufficient flushant is supplied to prevent the formation of clots within the internal axial bore 18 of the catheter 14. Periodically, the plug 52 is pulled by means of the tail 58 to permit the flushant to flow at a higher flow rate through the high velocity chamber 50 and the catheter 14. This high velocity pulse of flushant is selected to flow through the catheter 14 at a sufficient rate to overcome the opposing blood flow and flow past the probe tip 36 to wash away substantially all incipient clots that may have formed thereon.

The period between the pulses of high velocity flushant can be set in the range of once every 10 minutes to once every 3 hours. The velocity of the pulse is preferably in the range of 100 centimeters per second to 600 centimeters per second, or roughly 6 to 50 times the velocity of blood flowing in the blood vessels. The supply pressure is typically around 300 millimeters of mercury. The foregoing ranges are contemplated to be operative to whatever its advantage is in the application, e.g., whether used arterially or venously or inserted upstream or downstream with respect to blood flow. Furthermore, the velocity of blood flow is a well-known parameter, whether arterial, venous, human or animal.

Illustrated below in TABLE I are typical velocities and volumes for a probe inserted within a 20 gauge radial artery catheter falling within the ranges discussed above.

TABLE I
TYPICAL VELOCITIES AND VOLUMES FOR PROBE IN 20 GAUGE RADIAL ARTERY CATHETER

| FLUID & VESSEL | INTERNAL DIAMETER AREA (mm) | CROSS-SECTIONAL (mm$^2$) | FLOW VELOCITY (cm/sec) | RATE (ml/min) |
|---|---|---|---|---|
| Blood, radial artery | 2-4 | 3-13 | 6-55 | 50-100 |
| Low velocity flush in 20 ga catheter | 0.8 | 0.3* | .3-.4 | .05-.08 |
| High velocity flush in 20 ga catheter (short duration) | 0.8 | 0.3* | 330 | 60 |

(*Net area of catheter excluding probe)

A 20 gauge catheter will have approximately a 800 micron inside diameter. The probe sheath 40 of Table I has approximately a 450 micron outside diameter. The ribs 64 (not used in Table I) would project another 100 microns in each direction.

TABLE II below illustrates the relative volume contributions of the low velocity flush and the pulse of high velocity flush for the catheter of Table I.

TABLE II
RELATIVE VOLUME CONTRIBUTIONS OF LOW VELOCITY FLUSH AND HIGH VELOCITY FLUSH

| FLOW VELOCITY | DURATION (sec) | PERIOD (min) | PEAK DUTY FACTOR | TIME FLOW (ml/min) | AVG FLOW (ml/min) |
|---|---|---|---|---|---|
| "LOW" | CONTINUOUS | | 100% | .05-.08 | .05-.08 |
| "HIGH" | 1.0 | 10 | 0.2% | 60 | .10 |

The high volume flush shown in TABLE II is to be applied intermittently, for example, for a 1 second duration every 10 minutes. The "duty factor" of this flush (the duration divided by the period) determines how much contribution the high velocity component makes to the total fluid load. TABLE II also shows that the high velocity example from TABLE I produces up to 20% more volume than that of the low velocity background flush.

The parameters of each of the flushes can be altered to suit volume control needs. One reason for doing this would be to control the total dosage of a fluid-borne antithrombogenic drug, such as heparin. Another reason for altering the volume control is that the maximum instantaneous volume of an upstream pulse of high velocity flush should not exceed approximately 6 milliliters to avoid the possibility of forcing a clot upstream into the heart should the artery distal to the probe and catheter be occluded.

The response time of the sensors 38 to changing blood gases is approximately 2-4 minutes to 90% of final value. The 1 second duration pulse will, therefore, be filtered by the sensor's response and would be cleared rapidly by normally flowing blood. The resulting error is bounded by the duty factor and will be a relatively minor component of the total error factor for the system.

Animal tests using the method and apparatus for flushing clots of the present invention have demonstrated that velocities below the preferred range of 100 centimeters per second, or 6 times the blood flow velocity, permit clots to form within the internal axial bore 18 of the catheter 14. Conversely, velocities above the preferred range of 600 centimeters per second, or 50 times the blood flow velocity, result in a large and unacceptable error in the sensors.

While a preferred embodiment has been illustrated and described, it will be appreciated that various changes can be made therein without departing from the spirit and scope of the invention. For instance, the invention could be implemented with a manual or automated flush control. The automated flush control could be regulated with a computer such that a high velocity flush would be more frequently instituted during initial use of the probe 16, then reduced in frequency with time. Additionally, a signal processor attached to the connector 34 could be used to detect clot occurrences by monitoring the patterns, e.g., rate of change of signal shift from the sensor(s) 38 to distinguish between an incipient clot and a systemic parameter shift, thus prompting the timely application of a high velocity flush. Consequently, the invention can be practiced other than as specifically described herein.

The embodiments of the invention in which an exclusive property or privilege is claimed are defined as follows:

1. A process for flushing clots form an intravascular probe, comprising the steps of:
   inserting a catheter assembly in a blood vessel, the catheter assembly comprising a catheter segment having an internal axial bore, the segment fitted substantially throughout its bore with an intravascular probe, wherein the intravascular probe does not completely occlude the internal axial bore;
   delivering a flushant through the catheter bore and past the probe at a continual rate sufficient to maintain the catheter bore substantially free of blood clots; and periodically delivering through the catheter bore a pulse of flushant at a rate that is higher than the continual rate and effective to substantially clear the probe of incipient blood clots.

2. The process of claim 1, wherein the period is in the range of from about 10 minutes to about 3 hours.

3. The process of claim 1, wherein the ratio of the continual rate to the velocity of blood flow in the blood vessel is less than about 5%.

4. The process of claim 1, wherein the flow rate of the pulse of flushant is in the range of from about 6 to about 50 times the velocity of blood in the blood vessel.

5. The process of claim 1, wherein the flow rate of the pulse of flushant is in the range of from about 100 centimeters per second to about 600 centimeters per second.

6. The process of claim 1, wherein the catheter assembly comprises a centering means on the probe or the catheter or both for centering the probe within the catheter bore and providing fluid channels radially arrayed around the probe and axially arrayed along the catheter bore.

7. The process of claim 1, wherein the probe comprises at least one optical fiber.

8. The process of claim 1, wherein the probe comprises a thermocouple wire pair.

9. A hydrodynamic clot flushing system for flushing clots from an intravascular probe, the system comprising:

a catheter means insertable within an arterial or venous blood vessel, the catheter means having an internal axial bore for conducting fluid, said bore having therein means for supporting said probe and providing a space between said probe and the bore wall of the catheter to enable fluid to pass therethrough; and means for delivering a flushant through the internal axial bore of the catheter and past the probe at a first flow rate sufficient to maintain the internal axial bore of the catheter means substantially free of blood clots and a second flow rate that is higher than the first flow rate and effective to substantially clear the probe of incipient clots.

10. The system of claim 9, wherein the ratio of the first flow rate to the velocity of arterial or venous blood flow is less than about 5%.

11. The system of claim 9, wherein the second flow rate is in the range of from about 6 to about 50 times the velocity of blood in the blood vessel.

12. The system of claim 9, wherein the second flow rate is in the range of from about 100 centimeters per second to about 600 centimeters per second.

13. The system of claim 9, comprising means for centering the probe within the internal axial bore of the catheter means.

14. The system of claim 13, wherein the centering means comprises ribs formed on either of the probe or the catheter means or both for centering the probe within the internal axial bore and providing fluid channels radially arrayed around the probe and axially arrayed along the internal axial bore.

15. The system of claim 14, wherein the ratio of the first flow rate to the velocity of arterial or venous blood flow is less than about 5%.

16. The system of claim 14, wherein the second flow rate is in the range of from about 6 to about 50 times the velocity of blood in the blood vessel.

17. The system of claim 14, wherein the second flow rate is in the range of from about 100 centimeters per second to about 600 centimeters per second.

* * * * *

UNITED STATES PATENT AND TRADEMARK OFFICE
CERTIFICATE OF CORRECTION

PATENT NO. : 4,954,129

DATED : September 4, 1990

INVENTOR(S) : Giuliani et al.

It is certified that error appears in the above-identified patent and that said Letters Patent is hereby corrected as shown below:

On the title page, in the Abstract:

[57]  Line 9,   after "the" insert --first--

[57]  Line 11,  change "cather" to --catheter--

[57]  Line 12,  change "cather" to --catheter--

Signed and Sealed this

Seventh Day of April, 1992

Attest:

HARRY F. MANBECK, JR.

Attesting Officer

Commissioner of Patents and Trademarks